United States Patent [19]

Behnke et al.

[11] Patent Number: 5,405,331

[45] Date of Patent: Apr. 11, 1995

[54] IV INJECTION SITE AND SYSTEM

[75] Inventors: Brett A. Behnke, Hastings; Gary A. Thill, White Bear Lake, both of Minn.

[73] Assignee: Minnesota Mining and Manufacturing Company, St. Paul, Minn.

[21] Appl. No.: 72,512

[22] Filed: Jun. 4, 1993

Related U.S. Application Data

[63] Continuation of Ser. No. 921,908, Jul. 29, 1992, Pat. No. 5,300,034.

[51] Int. Cl.⁶ .............................................. A61M 5/178
[52] U.S. Cl. ..................................... 604/167; 604/246; 604/256; 137/844; 251/149.7
[58] Field of Search .................. 604/30, 33, 83, 86, 604/88, 91, 246, 247, 249, 256, 283–284, 167, 169; 215/247, 294, 355, DIG. 3; 251/149, 149.7; 137/800, 844–845

[56] References Cited

U.S. PATENT DOCUMENTS

| | | | |
|---|---|---|---|
| 2,546,672 | 3/1951 | LeClair | 251/149.7 |
| 3,977,400 | 8/1976 | Moorehead | 604/169 X |
| 4,294,249 | 10/1981 | Sheehan et al. | 128/214 |
| 4,857,062 | 8/1989 | Russell | 604/256 |
| 5,203,775 | 4/1993 | Frank et al. | 604/256 |
| 5,211,634 | 5/1993 | Vaillancourt | 604/167 |
| 5,215,537 | 6/1993 | Lynn et al. | 604/244 |
| 5,242,393 | 9/1993 | Brimhall et al. | 604/86 |

FOREIGN PATENT DOCUMENTS

| | | | |
|---|---|---|---|
| 0344907 | 12/1989 | European Pat. Off. | A61M 25/00 |
| 0413386 | 2/1991 | European Pat. Off. | A61M 5/14 |
| 8425197 U | 10/1985 | Germany | A61M 5/00 |
| WO90/11103 | 10/1990 | WIPO | A61M 39/00 |
| WO91/07206 | 5/1991 | WIPO | A61M 39/00 |
| WO91/10459 | 7/1991 | WIPO | A61M 5/00 |
| WO94/03373 | 2/1994 | WIPO | B65D 51/00 |

Primary Examiner—C. Fred Rosenbaum
Assistant Examiner—Corrine Maglione
Attorney, Agent, or Firm—Gary L. Griswold; Walter N. Kirn; Stephen W. Bauer

[57] ABSTRACT

An IV injection site adapted to receive a blunt cannula. The injection site comprises a housing having a passageway extending inwardly from its outside end, and an elastomeric septum closely received in the passageway of the housing. The septum has a bore extending into the septum from the inside end of the septum but not through the septum, and a slit extending generally in the axial direction into the septum from the outside end of the septum to the bore. When a cannula is introduced through the slit of the septum, the elastomeric material of the septum is displaced into the bore of the septum to sealingly engage the cannula along the bore of the septum.

50 Claims, 3 Drawing Sheets

IV INJECTION SITE AND SYSTEM

This invention relates generally to infusion therapy and IV injection sites, and more particularly to an IV injection site adapted for use with a blunt cannula, and is a continuation of U.S. application No. 07/921,908, now U.S. Pat. No. 5,300,034, filed Jul. 29, 1992.

BACKGROUND OF THE INVENTION

In an effort to reduce the risk of transmitting infectious diseases, such as hepatitis and AIDS, via accidental needle sticks, various designs of IV injection sites have been developed that are adapted to receive a blunt cannula and/or shielded cannula. See, e.g., Special Report and Product Review, Needlestick-Prevention Devices, Health Devices, pages 154–180 (ECRI, Plymouth Meeting, Pa. 1991). One approach has been to employ a slit septum Y-site in which a slit elastomeric septum is compressed in the Y-site housing. A blunt cannula can be introduced through the slit of the septum, and assuming the design works as intended, the septum will seal against the cannula shaft. When the cannula is removed, the septum seals itself.

Injection sites of this type are either available from or publicized by Baxter International, Inc., Deerfield, Ill., under the trade designation "Baxter's Needle-Less Injection Sites"; Abbott Laboratories, Inc., Abbott Park, Ill., under the trade designation "LifeShield Infection Control System"; and Kendall McGaw Laboratories, Inc., Irvine, Calif., under the trade designation "Safe-Line No-Needle I.V. System". A blunt cannula has been available from Becton, Dickinson and Company, Paramus, N.J., under the trade designation "Interlink System".

One problem with these systems is that they are sometimes incompatible. Some slit septum systems have permitted leakage either when a cannula is inserted or when no cannula has been inserted. In at least one slit septum site, it is possible to upset the septum in its housing by using an unspecified cannula or attempting to insert the cannula through the material of the septum somewhere other than through the slit.

SUMMARY OF THE INVENTION

This invention provides an IV injection site, system and method for injecting an IV fluid through the site with a blunt cannula; in which the site is adapted to provide improved and reliable sealing of the cannula in the site; and in which the force required to insert the cannula into the site is fairly low.

Generally, the IV injection site of the invention comprises a housing having an outside end and a passageway extending inwardly from the outside end, the passageway defining an axial direction, and an elastomeric septum closely received in the passageway of the housing. The septum has inside and outside ends relative to the outside end of the housing, a bore extending into the septum from the inside end of the septum generally in the axial direction but not through the septum, and a slit extending generally in the axial direction into the septum from the outside end of the septum to the bore. The housing includes opposed inner and outer annular ledges defining a septum-receiving portion of the passageway. The inner ledge engages the inside end of the septum adjacent the periphery thereof, and the outer ledge engages the outside end of the septum adjacent the periphery thereof. The arrangement is such that when a cannula is introduced through the slit of the septum the elastomeric material of the septum expands into the bore of the septum to sealingly engage the cannula along the bore of the septum.

Preferably, the bore of the septum is larger than the diameter of the cannula before the cannula is introduced into the slit of the septum. The bore is decreased in cross section when the cannula is introduced through the slit by movement of the material of the septum such that the septum sealingly engages the cannula along its bore.

The arrangement is such that the bore and slit portions of the septum each provide a separate sealing action against the cannula. This is accomplished by directing the material displaced by the expansion of the slit toward the bore. The septum is also designed to reduce the risk of the septum being displaced or upset from its proper position in its housing.

Other features will be pointed out hereinafter.

BRIEF DESCRIPTION OF THE DRAWING

The invention will be further described with reference to the drawing wherein corresponding reference characters indicate corresponding parts throughout the several views of the drawing, and wherein.

DETAILED DESCRIPTION OF PREFERRED EMBODIMENTS

Figure 4:
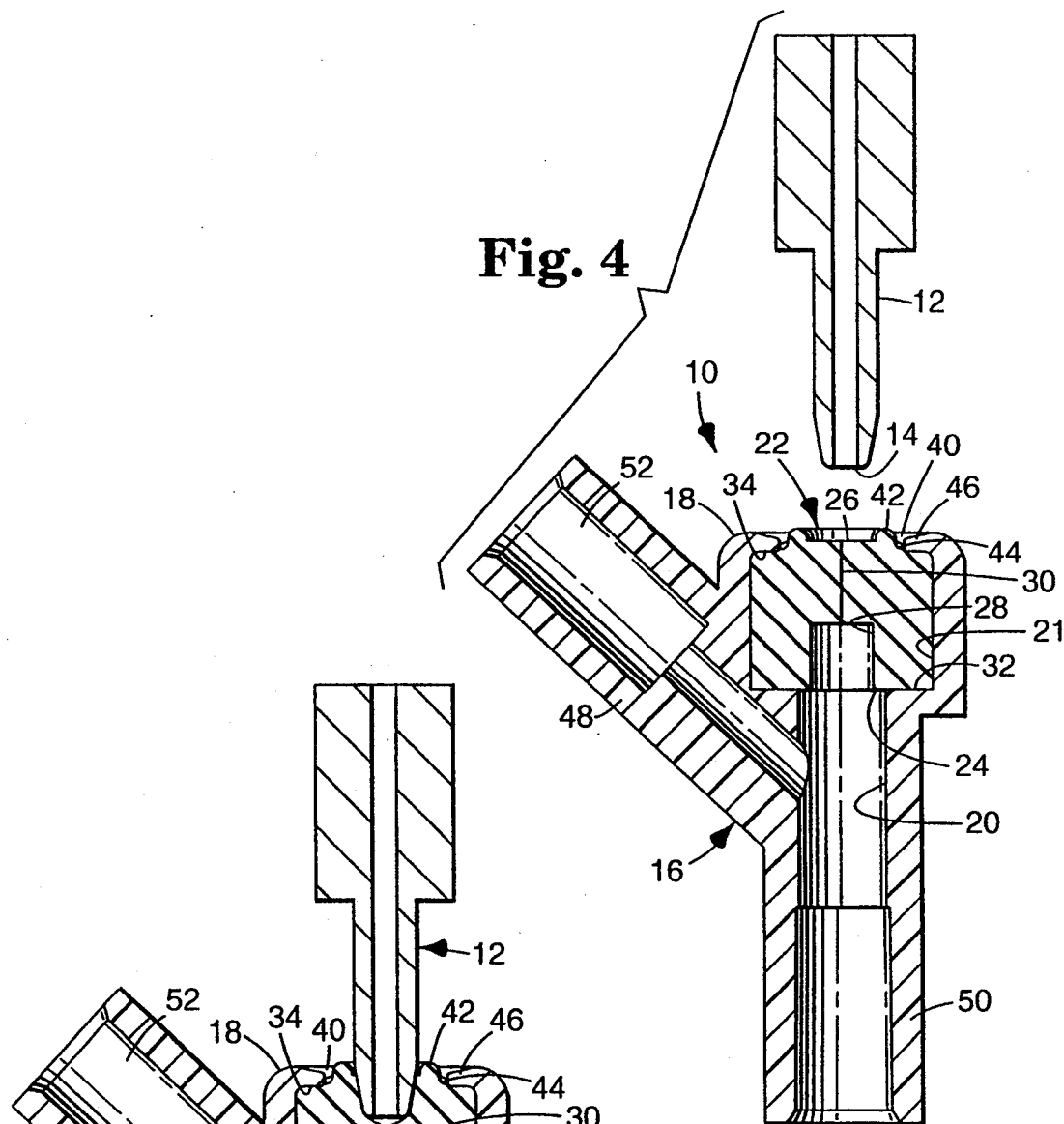
FIG. 4 is an enlarged cross-sectional view of the IV injection site of FIGS. 1 and 2 and a blunt cannula, showing the IV injection site before the cannula has been introduced therein.
Figure 5:
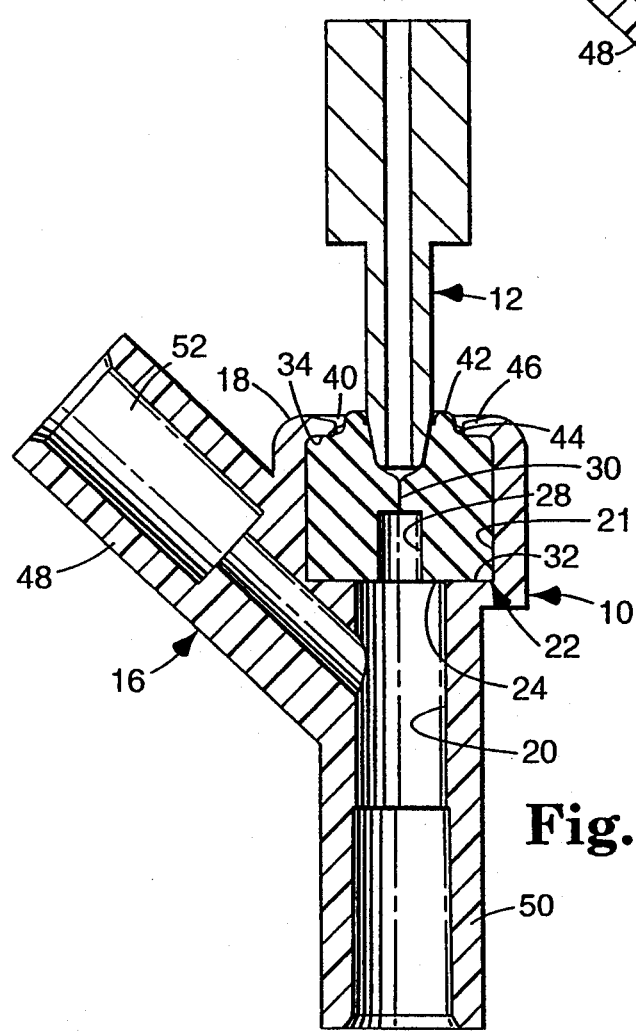
FIG. 5 is an enlarged cross-sectional view of the IV injection site and cannula of FIG. 4, showing the cannula partly inserted into the injection site.
Figure 6:
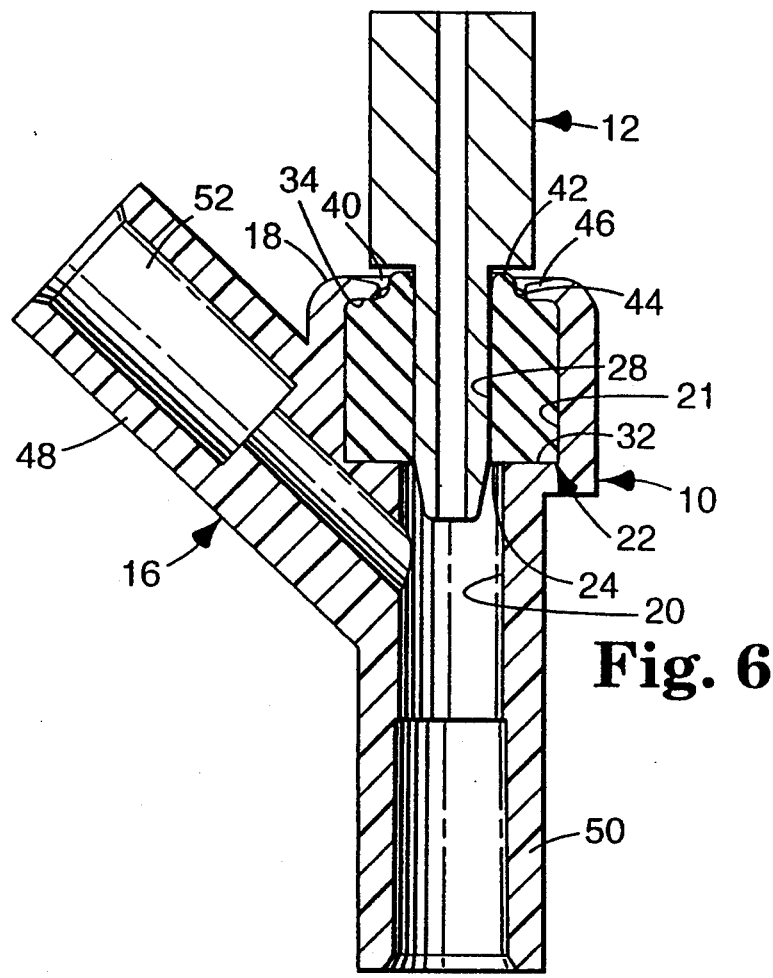
FIG. 6 is an enlarged cross-sectional view of the IV injection site and cannula of FIGS. 4 and 5, showing the cannula substantially completely inserted into the injection site.

Now referring to the drawing, an IV injection site of the invention is designated in its entirety by the reference numeral 10. The IV injection site 10 may be of the general type known as a Y-site, which provides a sealed port for injecting fluids into an IV tubing set (not shown). It is contemplated that the injection site 10 could be used in such IV administration tubing sets, drug vials, or other fluid systems involving medical fluids or a medical setting. The injection site 10 is particularly designed to be used with a blunt plastic or metal cannula 12 (FIGS. 4–6) that has a relatively smooth end 14 to reduce the risk to medical personnel of accidental needle sticks.

The injection site 10 generally comprises a housing 16 having an outside end 18 and a passageway 20 extending inwardly from the outside end 18. The passageway 20 defines an axial direction. An elastomeric septum 22 is closely received in the passageway 20 of the housing 16. The septum 22 has inside and outside ends 24 and 26 relative to the outside end 18 of the housing 16. A bore 28 extends into the septum 22 from the inside end 24 of the septum 22 generally in the axial direction but not through the septum 22, and a slit 30 extends generally in the axial direction into the septum 22 from the outside end 26 of the septum 22 to the bore 28.

The arrangement is such that, when a cannula 12 is introduced through the slit 30 of the septum 22, the elastomeric material of the septum 22 expands into the bore 28 of the septum 22 to sealingly engage the cannula 12 along the bore 28 of the septum 22.

The housing 16 includes opposed inner and outer annular ledges 32 and 34 defining a septum-receiving portion (also 20) of the passageway 20. The inner ledge 32 engages the inside end 24 of the septum 22 adjacent the periphery thereof, and the outer ledge 34 engages the outside end 26 of the septum 22 adjacent the periphery thereof. The septum-receiving portion 20 of the passageway 20 is generally cylindrical.

Figure 3:
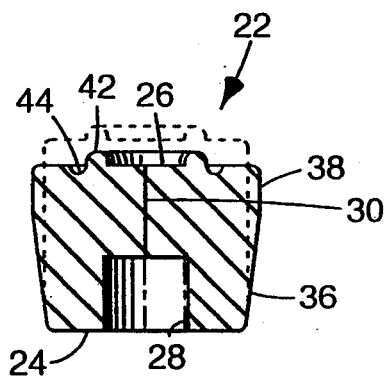
FIG. 3 is a cross-sectional view of the septum of FIG. 1, illustrating its configuration before it is assembled in the housing of the IV injection site.

Preferably, the septum 22 is formed, before being inserted in the housing 16 during assembly of the IV injection site 10, in a combined frustoconical/cylindrical configuration as illustrated in FIG. 3. The pre-assembly septum 22 includes a generally frustoconical portion 36 adjacent the inside end 24 of the septum 22 and tapering downwardly in the direction toward the inside end 24, and a generally constant diameter cylindrical portion 38 extending from the frustoconical portion 36 to the outside end 26 of the septum 22. The septum 22 is compressed radially by the housing 16 so as to have a generally cylindrical configuration after the septum 22 has been inserted in the housing 16 during assembly of the IV injection site 10.

Most preferably, the bore 28 of the septum 22 extends between 25–50% through the septum 22 and the slit 30 of the septum 22 extends between 50–75% through the septum 22, and the frustoconical portion 36 of the septum 22 extends a greater distance from the inside end 24 of the septum 22 than the bore 28 extends from the inside end 24 of the septum 22. As an illustrative example of the pre-assembly dimensions of the septum 22, the bore 28 may have a depth of approximately 0.105 inches (2.7 mm); the slit 30 may have a depth (axially along the septum 22) of approximately 0.129 inches (3.3 mm); the frustoconical portion 36 may have a length of approximately 0.164 inches (4 mm); and the cylindrical portion 38 may have a length of approximately 0.070 inches (1.8 mm). These dimensions change somewhat when the septum 22 is inserted into the housing 16 during assembly of the injection site 10.

The septum-receiving portion 20 of the passageway 20, which is defined as that portion 20 between the inner and outer ledges 32 and 34, is defined by a generally cylindrical wall (also 20) having a generally constant diameter.

The diameter of the septum-receiving portion 20 is most preferably greater than the smallest pre-assembly diameter of the frustoconical portion 36 of the septum 22 but smaller than the largest pre-assembly diameter of the frustoconical portion 36 or cylindrical portion 38 of the septum 22. For example, the diameter of the septum-receiving portion 20 of the housing 16 may be approximately 0.290 inches (7.4 mm); the pre-assembly diameter of the cylindrical portion 38, which equals the largest diameter of the frustoconical portion 36, may be approximately 0.322 inches (8.2 mm); and the smallest pre-assembly diameter of the frustoconical portion 36 may be approximately 0.280 inches (7.1 mm).

Figure 2:
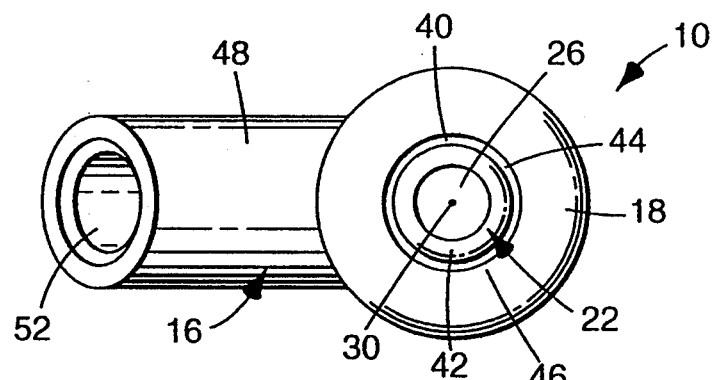
FIG. 2 is a top plan view of the IV injection site of FIG. 1.
Figure 1:
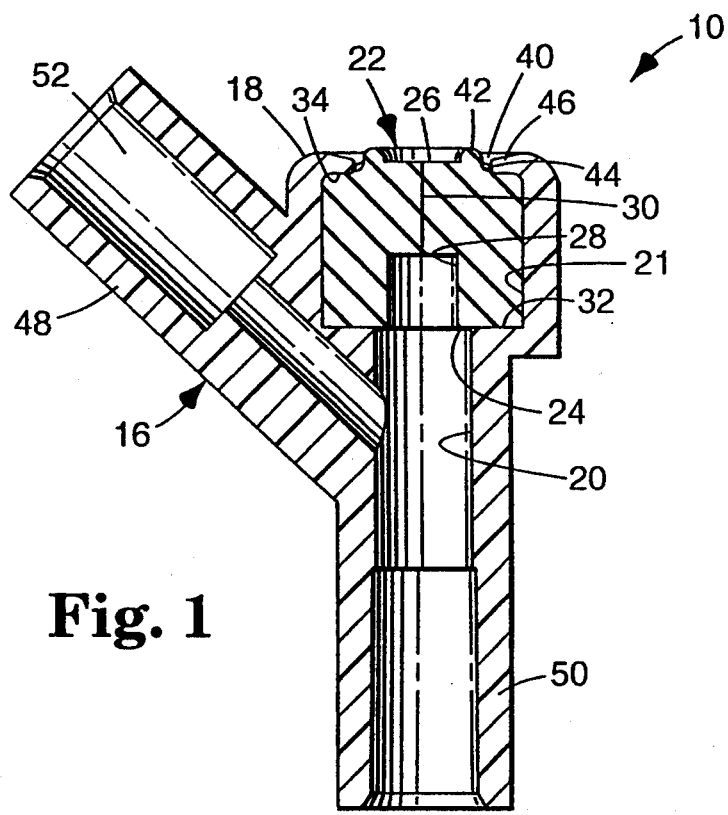
FIG. 1 is an enlarged cross-sectional view of the IV injection site, showing a novel septum and housing design.

The arrangement is such that the greatest compression is applied adjacent the outside end 26 of the septum 22. In the illustrative example provided above, the compression applied by the wall of the housing 16 against the cylindrical portion 38 reduces the diameter of the cylindrical portion approximately ten percent from its uncompressed configuration. FIG. 2 illustrates in phantom the configuration of the septum 22 after assembly in the housing 16.

The outer ledge 34 of the housing 16 defines a generally circular opening 40 where the outside end 26 of the septum 22 is exposed through the outside end 18 of the housing 16. The outside end 24 of the septum 22 includes an annular ridge 42 extending through the generally circular opening 40, and an annular channel 44 concentric with the annular ridge 42 and having a diameter greater than the diameter of the annular ridge 42. The outer ledge 34 has an annular inner edge 46 received in the annular channel 44 of the septum 22.

For example, the annular ridge 42 of the septum 22 may have an outer diameter of approximately 0.16 inches (4.1 mm) concentric with the central axis of the septum 22; an inner diameter of approximately 0.12 inches (3.0 mm); and a generally hemispherical cross-sectional configuration, with a cross-sectional radius of approximately 0.01 inches (0.25 mm).

The slit 30 is preferably formed in the molded septum 22 by cutting with a small blade (not shown), which may be inserted axially through the outside surface 26 of the septum 22. As an illustrative example, if the diameter of the cannula 12 most likely to be used in the septum 22 is approximately 0.05–0.10 inches (1.3–2.5 mm), the length of the slit 30 (laterally along the septum 22) may be approximately 0.03–0.08 inches (0.76–2.0 mm).

Most preferably, the slit-cutting blade (not shown) has a width of approximately 0.045 inches (1.14 mm) to cut a slit 30 having a length of approximately 0.045 inches (1.14 mm). This is believed to be optimum for use with the cannulae available under the trade designation "Needle-Less Injection Cannula" from Baxter International, Inc., Deerfield, Ill., as well as workable with the cannulae available from Abbott Laboratories, Inc., Abbott Park, Ill. under the trade designation "LifeShield Infection Control System". The outer diameter of Baxter's "Needle-Less Injection Cannula" is approximately 0.100 inches (2.5 mm), and the outer diameter of Abbott's "LifeShield" cannula is approximately 0.05 inches (1.27 mm).

Most preferably, the bore 28 of the septum 22 is larger than the diameter of the cannula 12 before the cannula 12 is introduced into the slit 30 of the septum 22. When the cannula 12 is introduced through the slit 30 (FIG. 5), the bore 28 of the septum is decreased in cross section by movement of the material of the septum 22 displaced by the cannula 12 such that the septum 22 sealingly engages the cannula 12 along the bore 28 of the septum 22.

For example, the bore 28 of the pre-assembly septum 22 preferably is generally cylindrical and has a diameter of approximately 0.120 inches (3.05 mm), which is believed to be optimum for a cannula 12 having a outside diameter of approximately 0.100 inches (2.5 mm). The bore 28 of the septum 22 is smaller after assembly of the injection site 10 than before due to compression of the septum 22 in the septum-receiving portion 20 of the housing 16.

The septum 22 is preferably integrally molded of a suitable elastomeric material, such as polyisoprene (natural or synthetic). The most preferred polyisoprene materials are synthetic, and have a durometer of approximately 35 on the Shore A scale and a compression set of approximately 16.4%. Suitable polyisoprene materials include "5218 or 5251 Gum Rubber" available from Abbott Laboratories, Inc., Abbott Park, Ill.; "1028 GUM Rubber" and Catalog Nos. "2-2-3 7389-35" and "2-6-2X 7389 -35" available from The West Company, Phoenixville, Pa.; and Catalog No. "L 3819" available from Neff Perkins Co., Painesville, Ohio. A silicone formulation available under Catalog No. "L 4795" from Neff Perkins Co., may also be suitable.

As used herein, "integrally molded" means molded in one continuous piece, as opposed to a number of pieces mechanically positioned together. The arrangement should be such that material displaced from the slit 30 is primarily directed to shrinking the diameter of the bore 28.

The housing 16 is preferably injection molded of a suitable synthetic resin material, such as acrylonitrile-butadiene-styrene (ABS). The material of the housing 16 is relatively un-yielding in normal use compared to the elastomeric material of the septum 22 so that the walls of the septum-receiving portion 20 of the passageway 20 do not expand significantly when the slit 30 is expanded by the cannula 12. The result is that the walls of the septum-receiving portion 20 of the passageway 20, as well as the inner and outer ledges 32 and 34, help direct the displaced material of the septum 22 to shrink the bore 28.

Most preferably, the outer ledge 34 is spin swaged to bend it inwardly over the outside end 26 of the septum 22 to hold the septum 22 in the housing 16. It is also contemplated that the outer ledge 34 could be ultrasonically deformed or deformed by a hot air/cold anvil process to bend it against the outside end 26 of the septum 22. Alternatively, the housing 16 could be molded in more than one piece that are assembled together to hold the septum 22 in place.

The IV injection site 10 may be in the form of a Y-site (also 10) as illustrated in the drawing, with an upstream arm 48, a downstream arm 50 and the septum-receiving portion 20. The inner walls of the upstream and downstream arms 48 and 50 define a lumen 52 extending in fluid communication with the passageway 20 along the inside end 24 of the septum 22. The upstream and downstream arms 48 and 50 are adapted to be mounted on the ends of conventional IV tubing (not shown).

The downstream arm 50 extends co-axially from the septum-receiving portion 20 so that insertion of the end 14 of the cannula 12 piercing the septum 22 is not stopped by the lumen-defining wall of the downstream arm 50. The downstream arm 50 preferably extends downwardly a distance from the outside end 26 of the septum 22 greater than the anticipated length of the cannula 12 to isolate the downstream section of IV tubing (not shown) from possible contact with the end 14 of the cannula 12.

The IV injection site 10 may be positioned along tubing sets of the types disclosed in co-assigned U.S. Pat. Nos. 4,236,880; 4,277,226; 4,322,201; 4,637,817; 4,673,390; 4,705,506; 4,714,463; and 5,017,192, which show infusion therapy systems and are incorporated herein by reference. In such a system, one injection site 10 could be positioned along the tubing set (not shown) upstream relative to an infusion pump (not shown) and another injection site 10 could be positioned along the tubing set downstream of the infusion pump.

The upstream IV injection site 10 provides a convenient mechanism to connect a second source of fluid into the multiple solution IV therapy systems disclosed in U.S. Pat. Nos. 4,637,817; 4,673,390; 4,705,506; and 4,714,463.

The injection site 10 can also be used in conventional gravity flow IV tubing sets (not shown) of the type designed to be used without an infusion pump, as well as with drug vials, or other medical injection sites.

Figure 7:
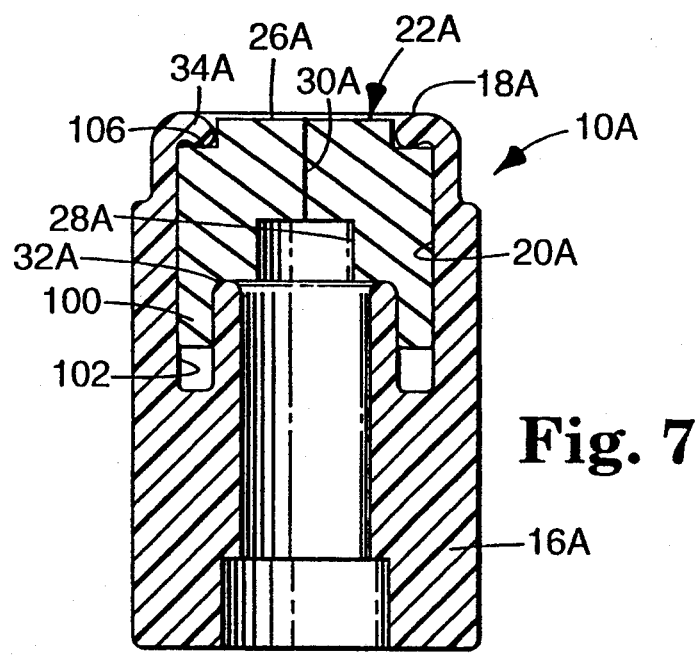
FIG. 7 is an enlarged cross-sectional view of an alternative embodiment of the IV injection site of the invention.

FIG. 7 illustrates an alternative embodiment of the IV injection site, here designated 10A, similar to injection site 10 but in which the inside end 24A of the septum 22A includes an annular skirt 100 extending axially inwardly from the septum 22A. (Reference numerals ending with an "A" in FIG. 7 designate parts designated in the other figures by the same reference numerals without the "A" ending.) The inner ledge 32A of the housing 16A includes an annular skirt-receiving channel 102 for receiving the skirt 100 of the septum 22A.

The skirt 100 and skirt-receiving channel 102 help stabilize the septum 22A in the housing 16A, and the relative dimensions of the skirt 100 and channel 102 facilitate fine tuning of the change in diameter of the bore 28A when a cannula 12 is inserted into the site 10A. As illustrated in FIG. 7, the channel 102 is deeper than the skirt 10 is long, providing space for expansion of the elastomeric material of the septum 22A when a cannula 12 expands the slit 30A, with the result that the diameter of the bore 28A would not shrink as much as the bore 28 of the injection site 10. The skirt-receiving channel 102 could alternatively have a length substantially equal to the length of the skirt 100 so that more of the material displaced by the cannula 12 piercing the slit 30A is directed to shrinking the diameter of the bore 28A.

The septum 22A of the alternative injection site 10A may also include an annular stepped shoulder 104 along the periphery of its outside end so that the outside end 18A of the housing 16A is approximately flush with the outside end 26A of the septum 22A. The outer ledge 34A may be ultrasonically crimped to retain the septum 22A in position.

It is also contemplated that the septum 22A would be tapered (possibly similarly to the septum 22) so that the greatest radial compression is provided adjacent the outside surface 26A of the septum 22A.

Although not preferred or shown, the septum-receiving portion may alternatively have a tapered configuration, with the smallest diameter being provided adjacent the outside end of the housing, to provide greater compression along the outside surface than elsewhere along the septum, although this arrangement results in more difficult assembly of the injection site. Assembling a multi-part housing (not shown) would be one way of manufacturing a housing having such a tapered septum-receiving portion. Such a multi-part housing may include one or more parts of a different color to indicate that the injection site is intended for use with a blunt cannula.

OPERATION

The operation of the IV injection site 10 will now be described. First, the cannula 12 is introduced into the slit 30 of the septum 22. As this is done, the cannula 12 expands the elastomeric material of the septum 22 to enlarge the slit 30 to receive the cannula 12. Since the material of the septum 22 is practically incompressible, the elastomeric material of the septum 22 displaced by the cannula 12 is directed by the housing 16 toward the bore 28 of the septum 22 to decrease the diameter of the bore 28. The diameter of the bore 28 of the septum 22 is decreased to less than or equal to the diameter of the cannula 12.

The cannula 12 is then introduced into the bore 28 of the septum 22 by continuing to insert the cannula 12 through the slit 30. This results in the septum 22 sealingly engaging the cannula 12 along the bore 28 of the septum 22. Because the diameter of the bore 28 of the septum 22 had been decreased to less than or equal to the diameter of the cannula 12, the elastomeric material of the septum 22 along its bore 28 presses against the cannula 12 when the cannula 12 is introduced into the bore 28 of the septum 22.

When the cannula 12 is removed from the injection site 10, the septum 22 returns to its normal configuration, with the slit 30 sealing against leakage.

As various changes could be made in the above constructions and methods without departing from the scope of the invention, it is intended that all matter contained in the above description or shown in the accompanying drawing be interpreted as illustrative and not in a limiting sense.

We claim:

1. A self-sealing, cannula-receiving site adapted to sealingly receive a blunt cannula, the site comprising:
   a housing having an outside end and a passageway extending inwardly from the outside end, the passageway defining an axial direction and having a septum-receiving portion that is generally cylindrical;
   an elastomeric septum closely received in the passageway of the housing, the septum having inside and outside ends relative to the outside end of the housing, the septum including a slit, extending into the septum from the outside end of the septum generally in the axial direction for sealing the outside end of the housing;
   the septum being formed, before being inserted into the septum-receiving portion of the passageway of the housing during assembly of the site, in a configuration including a generally frustoconical portion adjacent the inside end of the septum and tapering downwardly in the direction toward the inside end, with the septum being compressed radially by the housing so as to have a generally cylindrical configuration after the septum has been inserted into the housing during assembly of the site.

2. A self-sealing, cannula-receiving site according to claim 1 wherein the septum-receiving portion of the passageway is defined by a wall having a generally constant diameter greater than the smallest pre-assembly diameter of the frustoconical portion of the septum but smaller than the largest pre-assembly diameter of the frustoconical portion of the septum.

3. A self-sealing, cannula-receiving site according to claim 2 wherein before assembly of the site the septum includes a generally constant diameter cylindrical portion extending from the frustoconical portion to the outside end of the septum.

4. A self-sealing, cannula-receiving site according to claim 1 wherein the housing further comprises opposed inner and outer annular ledges defining the septum-receiving portion of the passageway, the inner annular ledge engaging the inside end of the septum adjacent the periphery thereof, and the outer annular ledge engaging the outside end of the septum adjacent the periphery thereof.

5. A self-sealing, cannula-receiving site according to claim 4 wherein the outer ledge defines a generally circular opening through the outside end of the housing where the outside end of the septum is exposed.

6. A self-sealing, cannula-receiving site according to claim 5 wherein the outer ledge is formed by swaging the outer end of the housing over the septum.

7. A self-sealing, cannula-receiving site according to claim 1 wherein the site comprises an IV injection Y-site on an IV tubing set.

8. A self-sealing, cannula-receiving site according to claim 1 wherein the housing is formed of synthetic resin material.

9. A self-sealing, cannula-receiving site adapted to sealingly receive a blunt cannula, the site comprising:
   a housing having an outside end and a passageway extending inwardly from the outside end, the passageway defining an axial direction;
   an elastomeric septum closely received in the passageway of the housing, the septum having inside and outside ends relative to the outside end of the housing;
   the serum including a slit, extending into the septum from the outside end of the septum generally in the axial direction but not through the septum, for sealing the outside end of the housing; and a bore, extending into the septum from the inside end of the septum generally in the axial direction substantially to the slit, for sealingly engaging a blunt cannula inserted through the slit into the bore; and
   means in the housing for diverting elastomeric material of the septum displaced when a cannula is inserted into the slit into the bore to sealingly engage the cannula along the bore;
   the passageway of the housing having a septum-receiving portion that is generally cylindrical; the septum being formed, before being inserted into the housing during assembly of the site, in a configuration including a generally frustoconical portion adjacent the inside end of the septum and tapering downwardly in the direction toward the inside end, with the septum being compressed radially by the housing so as to have a generally cylindrical configuration after the septum has been inserted into the housing during assembly of the site.

10. A self-sealing, cannula-receiving site according to claim 22 wherein the housing is formed of synthetic resin material.

11. A self-sealing, cannula-receiving site according to claim 9 wherein the septum-receiving portion of the passageway is defined by a wall having a generally constant diameter greater than the smallest pre-assembly diameter of the frustoconical portion of the septum but smaller than the largest pre-assembly diameter of the frustoconical portion of the septum.

12. A self-sealing, cannula-receiving site according to claim 11 wherein before assembly of the site the septum includes a generally constant diameter cylindrical portion extending from the frustoconical portion to the outside end of the septum.

13. A self-sealing, cannula-receiving site according to claim 11 wherein the means for diverting elastomeric material of the septum includes the wall defining the septum-receiving portion of the passageway of the housing.

14. A self-sealing, cannula-receiving site according to claim 13 wherein the means for diverting the elastomeric material of the septum further includes opposed inner and outer ledges defining the septum-receiving portion of the passageway.

15. A self-sealing, cannula-receiving site according to claim 14 wherein the inner ledge engages the inside end of the septum adjacent the periphery thereof, and the outer ledge engages the outside end of the septum adjacent the periphery thereof, the inner and outer ledges each being generally annular.

16. A self-sealing, cannula-receiving site according to claim 15 wherein the outer ledge defines a generally circular opening through the outside end of the housing where the outside end of the septum is exposed.

17. A self-sealing, cannula-receiving site according to claim 9 wherein the bore of the septum extends between 25–50% through the septum, and the slit of the septum extends between 50–75% through the septum.

18. A self-sealing, cannula-receiving site according to claim 9 wherein the site comprises an IV injection Y-site on an IV tubing set.

19. An IV tubing set having a self-sealing, cannula-receiving site adapted to sealingly receive a blunt cannula, the site comprising:
  a housing having an outside end and a passageway extending inwardly from the outside end, the passageway defining an axial direction;
  an elastomeric septum closely received in the passageway of the housing, the septum having inside and outside ends relative to the outside end of the housing;
  the septum including a slit, extending into the septum from the outside end of the septum generally in the axial direction but not through the septum, for sealing the outside end of the housing; and a bore, extending into the septum from the inside end of the septum generally in the axial direction substantially to the slit, for sealingly engaging a blunt cannula inserted through the slit into the bore; and
  means in the housing for diverting elastomeric material of the septum displaced when a cannula is inserted into the slit to the bore to sealingly engage the cannula along the bore;
  the passageway of the housing having a septum-receiving portion that is generally cylindrical; the septum being formed, before being inserted into the housing during assembly of the site, in a configuration including a generally frustoconical portion adjacent the inside end of the septum and tapering downwardly in the direction toward the inside end, with the septum being compressed radially by the housing so as to have a generally cylindrical configuration after the septum has been inserted into the housing during assembly of the site.

20. An IV tubing set according to claim 19 wherein the housing is formed of synthetic resin material.

21. An IV tubing set according to claim 19 wherein the septum-receiving portion of the passageway is defined by a wall having a generally constant diameter greater than the smallest pre-assembly diameter of the frustoconical portion of the septum but smaller than the largest pre-assembly diameter of the frustoconical portion of the septum.

22. An IV tubing set according to claim 21 wherein before assembly of the site the septum includes a generally constant diameter cylindrical portion extending from the frustoconical portion to the outside end of the septum.

23. An IV tubing set according to claim 21 wherein the means for diverting elastomeric material of the septum includes the wall defining the septum-receiving portion of the passageway of the housing.

24. An IV tubing set according to claim 23 wherein the means for diverting the elastomeric material of the septum further includes opposed inner and outer ledges defining the septum-receiving portion of the passageway.

25. An IV tubing set according to claim 24 wherein the inner ledge engages the inside end of the septum adjacent the periphery thereof, and the outer ledge engages the outside end of the septum adjacent the periphery thereof, the inner and outer ledges each being generally annular.

26. An IV tubing set according to claim 25 wherein the outer ledge defines a generally circular opening through the outside end of the housing where the outside end of the septum is exposed.

27. An IV tubing set according to claim 19 wherein the bore of the septum extends between 25–50% through the septum, and the slit of the septum extends between 50–75% through the septum.

28. An IV tubing set according to claim 19 wherein the site comprises an IV injection Y-site mounted on the IV tubing set.

29. A connection system comprising a blunt cannula and a self-sealing, cannula-receiving site adapted to sealingly receive the blunt cannula, the site comprising:
  a housing having an outside end and a passageway extending inwardly from the outside end, the passageway defining an axial direction;
  an elastomeric septum closely received in the passageway of the housing, the septum having inside and outside ends relative to the outside end of the housing;
  the septum including a slit, extending into the septum from the outside end of the septum generally in the axial direction but not through the septum, for sealing the outside end of the housing; and a bore, extending into the septum from the inside end of the septum generally in the axial direction substantially to the slit, for sealingly engaging the blunt cannula inserted through the slit into the bore; and
  means in the housing for diverting elastomeric material of the septum displaced when the cannula is inserted into the slit into the bore to sealingly engage the cannula along the bore;
  the passageway of the housing having a septum-receiving portion that is generally cylindrical; the septum being formed, before being inserted into the housing during assembly of the site, in a configuration including a generally frustoconical portion adjacent the inside end of the septum and tapering downwardly in the direction toward the inside end, with the septum being compressed radially by the housing so as to have a generally cylindrical configuration after the septum has been inserted into the housing during assembly of the site.

30. A connection system according to claim 32 wherein the housing is formed of synthetic resin material.

31. A connection system according to claim 29 wherein the septum-receiving portion of the passageway is defined by a wall having a generally constant diameter greater than the smallest pre-assembly diameter of the frustoconical portion of the septum but smaller than the largest pre-assembly diameter of the frustoconical portion of the septum.

32. A connection system according to claim 31 wherein before assembly of the site the septum includes a generally constant diameter cylindrical portion extending from the frustoconical portion to the outside end of the septum.

33. A connection system according to claim 31 wherein the means for diverting elastomeric material of the septum includes the wall defining the septum-receiving portion of the passageway of the housing.

34. A connection system according to claim 33 wherein the means for diverting the elastomeric material of the septum further includes opposed inner and outer ledges defining the septum-receiving portion of the passageway.

35. A connection system according to claim 34 wherein the inner ledge engages the inside end of the septum adjacent the periphery thereof, and the outer ledge engages the outside end of the septum adjacent the periphery thereof, the inner and outer ledges each being generally annular.

36. A connection system according to claim 35 wherein the outer ledge defines a generally circular opening through the outside end of the housing where the outside end of the septum is exposed.

37. A connection system according to claim 29 wherein the bore of the septum extends between 25-50% through the septum, and the slit of the septum extends between 50-75% through the septum.

38. A connection system according to claim 29 wherein the site comprises an IV injection Y-site on an IV tubing set.

39. A connection system according to claim 29 wherein the cannula is generally cylindrical having a diameter, the bore of the septum having a cross section that before insertion of the cannula into the slit has a diameter greater than the diameter of the cannula, the bore being decreased in cross section when the cannula is inserted through the slit by movement of the elastomeric material of the septum such that the septum sealingly engages the cannula along the bore of the septum.

40. A connection system comprising a blunt cannula and an IV tubing set having a self-sealing, cannula-receiving site adapted to sealingly receive the blunt cannula, the site comprising:
 a housing having an outside end and a passageway extending inwardly from the outside end, the passageway defining an axial direction;
 an elastomeric septum closely received in the passageway of the housing, the septum having inside and outside ends relative to the outside end of the housing;
 the septum including slit means, extending into the septum from the outside end of the septum generally in the axial direction but not through the septum, for sealing the outside end of the housing; and bore means, extending into the septum from the inside end of the septum generally in the axial direction substantially to the slit means, for sealingly engaging the blunt cannula inserted through the slit means into the bore means; and
 means in the housing for diverting elastomeric material of the septum displaced when the cannula is inserted into the means into the bore means to sealingly engage the cannula along the bore means;
 the passageway of the housing having a septum-receiving portion that is generally cylindrical; the septum being formed, before being inserted into the housing during assembly of the site, in a configuration including a generally frustoconical portion adjacent the inside end of the septum and tapering downwardly in the direction toward the inside end, with the septum being compressed radially by the housing so as to have a generally cylindrical configuration after the septum has been inserted into the housing during assembly of the site.

41. A connection system according to claim 19 wherein the housing is formed of synthetic resin material.

42. A connection system according to claim 40 wherein the septum-receiving portion of the passageway is defined by a wall having a generally constant diameter greater than the smallest pre-assembly diameter of the frustoconical portion of the septum but smaller than the largest pre-assembly diameter of the frustoconical portion of the septum.

43. A connection system according to claim 42 wherein before assembly of the site the septum includes a generally constant diameter cylindrical portion extending from the frustoconical portion to the outside end of the septum.

44. A connection system according to claim 42 wherein the means for diverting elastomeric material of the septum includes the wall defining the septum-receiving portion of the passageway of the housing.

45. A connection system according to claim 44 wherein the means for diverting the elastomeric material of the septum further includes opposed inner and outer ledges defining the septum-receiving portion of the passageway.

46. A connection system according to claim 45 wherein the inner ledge engages the inside end of the septum adjacent the periphery thereof, and the outer ledge engages the outside end of the septum adjacent the periphery thereof, the inner and outer ledges each being generally annular.

47. A connection system according to claim 46 wherein the outer ledge defines a generally circular opening through the outside end of the housing where the outside end of the septum is exposed.

48. A connection system according to claim 40 wherein the site comprises an IV injection Y-site mounted on the IV tubing set.

49. A connection system according to claim 40 wherein the cannula is generally cylindrical having a diameter, the bore means of the septum comprising a bore that before insertion of the cannula into the slit means has a diameter greater than the diameter of the cannula, the bore being decreased in cross section when the cannula is inserted through the slit means by movement of the elastomeric material of the septum such that the septum sealingly engages the cannula along the bore of the septum.

50. A connection system according to claim 19 wherein the bore means of the septum extends between 25-50% through the septum, and the slit means of the septum extends between 50-75% through the septum.

* * * * *

UNITED STATES PATENT AND TRADEMARK OFFICE
CERTIFICATE OF CORRECTION

PATENT NO. : 5,405,331
DATED : April 11, 1995
INVENTOR(S) : Brett A. Behnke and Gary A. Thill It is certified that error appears in the above-indentified patent and that said Letters Patent is hereby corrected as shown below:

Col. 8, line 50, "22" should read --9--.

Signed and Sealed this

Twenty-first Day of November, 1995

Attest:

BRUCE LEHMAN

*Attesting Officer*   *Commissioner of Patents and Trademarks*